United States Patent [19]

Clarke et al.

[11] 4,233,448

[45] Nov. 11, 1980

[54] 3-METHOXYCARBONYL-2-(2-THIENYL)-8-AZABICYCLO[3.2.1]OCTANE-8-ACETAMIDE AND SALTS THEREOF

[75] Inventors: Robert L. Clarke, Bethlehem; Sol J. Daum, Albany, both of N.Y.

[73] Assignee: Sterling Drug Inc., New York, N.Y.

[21] Appl. No.: 88,537

[22] Filed: Oct. 26, 1979

Related U.S. Application Data

[62] Division of Ser. No. 41,907, May 24, 1979, which is a division of Ser. No. 894,894, Apr. 10, 1978, Pat. No. 4,179,567.

[51] Int. Cl.³ .......................................... C07D 471/08
[52] U.S. Cl. ...................................................... 546/125
[58] Field of Search ......................................... 546/125

[56] References Cited

U.S. PATENT DOCUMENTS 3,813,404   5/1974   Clarke et al. ...................... 546/125

OTHER PUBLICATIONS

Kan-Fan et al., Acta Chemica Scand., vol. 27, No. 3, pp. 1039–1052 (1973).

*Primary Examiner*—Alan L. Rotman
*Attorney, Agent, or Firm*—Thomas L. Johnson; B. Woodrow Wyatt

[57] ABSTRACT

Compounds of the tropane (8-azabicyclo[3.2.1]octane) series having an aromatic substitutent in the 2-position and a carboalkoxy group in the 3-position are prepared by reacting a tropane-3-carboxylate having a double bond in the 2,3-position with an aryl Grignard reagent. Transformations of the substituent on nitrogen are subsequently effected. Compounds where the 3-carboalkoxy group is in the exo configuration possess hypoglycemic activity, and those where the 3-carboalkoxy group is in the endo configuration possess narcotic antagonist activity.

1 Claim, No Drawings

3-METHOXYCARBONYL-2-(2-THIENYL)-8-AZABICYCLO[3.2.1]OCTANE-8-ACETAMIDE AND SALTS THEREOF

This application is a division of application Ser. No. 41,907, filed May 24, 1979, which is in turn a division of application Ser. No. 894,894, filed Apr. 10, 1978, now U.S. Pat. No. 4,179,567 issued Dec. 18, 1979.

BACKGROUND OF THE INVENTION (a) Field of the Invention

This invention relates to novel compounds of the tropane (8-azabicyclo[3.2.1]octane) series, in particular tropanes having an aromatic substituent in the 2-position and a carboalkoxy group in the 3-position.

(b) Description of the Prior Art

Clarke and Daum U.S. Pat. No. 3,813,404, issued May 28, 1974 discloses tropane derivatives having the formula:

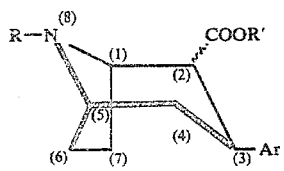

wherein Ar is phenyl or substituted phenyl, R is hydrogen or lower-alkyl, and R' is lower-alkyl. The compounds of the patent possess local anesthetic and central nervous system stimulant activities.

C. Kan-Fan et al., Acta Chemica Scand. 27, 1039 (1973), disclose an alkaloid isolated from a plant and having the structure:

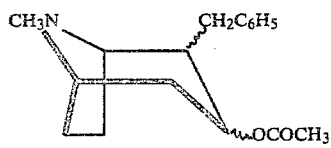

No physiological properties are disclosed for the latter compound in the reference.

SUMMARY OF THE INVENTION

In a composition of matter aspect, the invention relates to compounds of the formula:

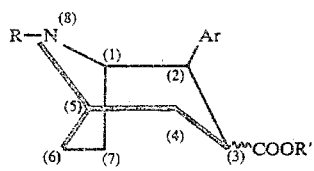

wherein:
R is selected from the group consisting of:
  hydrogen,
  alkyl of 1-8 carbon atoms optionally interrupted by an oxygen atom,
  phenylalkyl where alkyl has 1-3 carbon atoms,
  cyclopropylmethyl,
  hydroxyalkyl of 2-4 carbon atoms, and
  2,2-diethoxyethyl;
Ar is selected from the group consisting of:
  phenyl,
  benzyl,
  3-hydroxyphenyl,
  3-methoxyphenyl, and
  2-thienyl;
and R' is hydrogen or alkyl of 1 to 3 carbon atoms; or pharmaceutically acceptable acid-addition salts thereof. Also included are several related compounds which fall outside the scope of the definitions of R and Ar given above.

In a further composition of matter aspect, the invention relates to compounds of the formula:

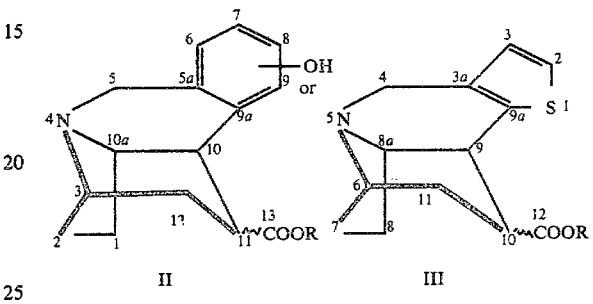

wherein R is alkyl of 1 to 3 carbon atoms, and the hydroxy group of II is in the 6- or 8-position of the pyrrolo[1,2-b]isoquinoline ring; or pharmaceutically acceptable acid-addition salts thereof. The compounds of Formulas II and III can be considered as variants of the compounds of Formula I wherein the group R represents a methylene bridge between the nitrogen atom and the aromatic nucleus.

In a process aspect, the invention relates to a process for preparing a compound of Formula I which comprises reacting a compund of the formula:

with ArMgX, where X is chlorine, bromine or iodine in an inert organic solvent under anhydrous conditions.

In a further process aspect, the invention relates to a process for preparing a compund of Formula I where R is other than hydrogen which comprises reacting a compound of Formula I where R is hydrogen with RX, where X is chlorine, bromine or iodine, in an inert organic solvent in the presence of a base.

DETAILED DESCRIPTION INCLUSIVE OF PREFERRED EMBODIMENTS

If derived by synthesis from natural sources, the compounds of the invention will be optically active. However, optically inactive racemic mixtures can be obtained by total synthesis and these in turn can be resolved by conventional procedures to obtain both optical isomers, one being identical to the enantiomer (1R) obtained from natural sources and the other the "unnatural" enantiomer (1S).

The compounds of Formulas I, II and III and related species are useful both in the free base forms and in the form of acid-addition salts, and both forms are within the purview of the invention.

The acid-addition salts are simply a more convenient, water-soluble form for use, and in practice, use of the salt form inherently amounts to use of the base form. For pharmaceutical purposes, the acids which can be used to prepare the acid-addition salts include preferably those which produce, when combined with the free base, pharmaceutically acceptable salts, that is, salts whose anions are relatively innocuous to the animal organism in medicinal doses of the salts, so that the beneficial properties inherent in the free base are not vitiated by side-effects ascribable to the anions. Appropriate pharmaceutically acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

The compounds can be prepared for use by dissolving under sterile conditions salt forms of the compounds in water (or an equivalent amount of a non-toxic acid if the free base is used), or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like.

The molecular structures of the compounds of this invention were assigned on the basis of the methods of their synthesis and the study of their infrared and nuclear magnetic resonance (NMR) spectra, and confirmed by the correspondence between calculated and found values for the elementary analyses for representative examples.

The compounds of Formula I can be prepared by reacting a compound of the Formula IV with Ar-magnesium halide, where the halide is chloride, bromide or iodide, in an inert organic solvent under anhydrous conditions.

A preferred starting material is the known compound of Formula IV where R and R' are methyl.

The reaction of a compound of Formula IV with a Grignard reagent produces a mixture of two isomers of Formula I wherein the 3-carboalkoxy group is in the exo (beta or equatorial) configuration and the endo (alpha or axial) configuration which can be separated by fractional crystallization and/or column or plate chromatography.

Under basic conditions, as with sodium methoxide in methanol, equilibration of the epimers of Formula I occurs in which the exo epimer is preferentially formed. Thus the endo epimers can serve as intermediates for the exo epimers.

The compounds of Formula I or IV where R is hydrogen are prepared by differing methods, depending upon the nature of the Ar substituent. Because of steric hindrance, compounds of Formula I where R is methyl and Ar is phenyl or substituted phenyl are not readily demethylated by conventional means using such reagents as ethyl chloroformate or cyanogen bromide. Alternatively, these compounds are prepared by debenzylation of the compounds of Formula I where R is benzyl and Ar is phenyl or substituted phenyl. The debenzylation is carried out by catalytic hydrogenolysis. The debenzylation procedure cannot be used to prepare compounds of Formula I where R is hydrogen and Ar is 2-thienyl because the presence of sulfur poisons the catalyst. Fortunately, however, in this instance the ethyl diazoacetate N-demethylation procedure can be used, provided the diazoacetate adduct is hydrolyzed in a manner to avoid cyclization to form a compound of Formula III. A preferred hydrolysis reagent is hydrogen iodide in pyridine. In the event methanolic hydrochloric acid is used as the hydrolysis medium, the primary product is the cyclized compound III. Cyclized products of Formula II are prepared by an analogous procedure.

The compounds of Formula I where R is other than hydrogen or methyl can be prepared by alkylation of the compounds where R is hydrogen with R-X, where X is halogen, preferably bromine or iodine, in the presence of a base.

The compounds of Formula I can be further reacted with methylmagnesium halide to produce ketones wherein the 3-carboalkoxy group of Formula I is replaced by an acetyl group.

Pharmacological evaluation of the compounds of Formula I has shown that those wherein the 3-carboalkoxy group is in the exo (beta or equatorial) configuration possess hypoglycemic activity upon oral administration to experimental animals, the activity residing in the 1R optical enantiomer. The compounds are thus useful in counteracting high blood sugar levels such as are present in diabetic conditions.

The hypoglycemic activity in these compounds is accompanied by varying degrees of analgesic activity. This is an undesirable side-effect, but it can be counteracted by subcutaneous administration of a narcotic antagonist such as nalorphine prior to giving the hypoglycemic agent.

Hypoglycemic activity has also been found in compounds corresponding to Formula I wherein the equatorial 3-carboalkoxy group is replaced by an acetyl group; and in compounds of Formulas II and III when the carboalkoxy group is in the exo (equatorial) position.

The hypoglycemic activity was measured in fasted 100 g male Sprague-Dawley rats given either water or the test compound in water alone or with glucose (3 mg/kg orally) or with glucose plus glucagon (3 mg/kg subcutaneously). Blood samples were obtained from the tail vein at 0, 0.5, 1, 1.5 and 2 hours after treatment and were analyzed for glucose using a Technicon Auto Analyzer. By this procedure the compounds of Formula I of the exo configuration reduced the glucose blood levels by amounts varying from 20 to 80 percent, depending upon the specific compound used, at dose levels of 64–100 mg/kg (calculated as free base, administered orally).

The analgesic activity was determined in rats by a modified D'Amour-Smith "tail flick" method described by Harris and Pierson, *J. Pharmacol. Exp. Ther.* 143, 141 (1964). Activities roughly equal to that of codeine were observed in the compounds of Formula I of the exo configuration. The analgesic activity was effectively blocked by administering 1 mg/kg of nalorphine subcutaneously 10 minutes prior to giving the test compound.

Pharmacological evaluation of the compounds of Formula I wherein the 3-carboalkoxy group is in the endo (alpha or axial) configuration has shown that they possess narcotic antagonist activity, devoid of demonstrable analgesic activity, and are thus useful in counteracting the effects of narcotics. The activity resides in the 1S optical enantiomer.

The narcotic antagonist activity was measured in rats by oral or subcutaneous administration according to the method of Harris and Pierson, loc. cit., using phenazocine, morphine or meperidine as the narcotic being antagonized. By this procedure the compounds of Formulas I and II of the endo configuration were shown to have narcotic antagonist activity vs pentazocine at $AD_{50}$ values ranging from 0.3 56 mg/kg upon subcutaneous as well as oral administration. The endo isomers are also effective as antagonists of the analgesic activity present in the exo isomers, without affecting the hypoglycemic activity in the latter. Thus, the mixture of exo and endo isomers, initially produced by the Grignard reaction, are useful as hypoglycemic agents without appreciable analgesic side-effects.

The following examples will further illustrate the invention without the latter being limited thereby.

EXAMPLE 1

Reaction of Methyl (1RS)-8-Methyl-8-azabicyclo[3.2.1]oct-2-ene-3-carboxylate with Phenylmagnesium Bromide (a) A solution of 48.5 g (0.268 mol) of compound IV (R and R' are methyl) in 200 ml of ether was added dropwise with stirring in 40 min. to 135 ml (0.40 mol) of 3M phenylmagnesium bromide (in ether) in 350 ml of ether, the internal temperature being held at $-23°\pm2°$ C. The mixture was stirred at this temperature for 1 hr. and then poured into 500 ml of 2N hydrochloric acid and 250 g of ice with vigorous stirring. The layers were separated and the water layer was washed with ether and made strongly alkaline with conc. ammonium hydroxide. Extraction with ether gave 68 g of oily product which was distilled. The products of interest (55.6 g) were collected at 116°–130° C. (0.25–0.35 mm). Gas chromatography (GC) showed a 52:48 ratio (3-exo:3-endo) of the major components. Dilution of this distillate with 50 ml of pentane and chilling gave 10.2 g of massive prisms. It was recrystallized twice by melting, dilution with 2 volumes of pentane, cooling and seeding to give methyl (1RS-exo,exo)-8-methyl-2-phenyl-8-azabicyclo[3.2.1]octane-3-carboxylate, m.p. 59°–61° C.; hydrochloride salt, m.p. 210°–211° C. (needles from acetone).

(b) A 6 portion of the oily residue remaining after separation of the 10.2 g of prisms above was chromatographed on 27 preparative silica gel plates using multiple passes of a 1.5:20:78.5 i-PrNH$_2$-Et$_2$O-pentane solvent system. The less polar of the two major bands furnished 1.56 g of the 3-exo ester described in part (a) above. The more polar band yielded 2.93 g of oily methyl (1RS-2-exo-3-endo)-8-methyl-2-phenyl-8-azabicyclo[3.2.1]octane-3-carboxylate. Its hydrochloride salt had the m.p. 227° C.(decompn.), colorless plates from acetonitrile.

EXAMPLE 2

(a) According to the procedure of Example 1, part (a), 18.1 g (0.10 mol) of compound IV (R and R' are methyl) was caused to react with a Grignard reagent prepared from 39.5 g (0.15 mol) of benzyl 3-bromophenyl ether, 4.9 g (0.20 g-atom) of magnesium and 200 ml of ether. The Grignard reagent and solvent formed 2 layers. The crude product was distilled rapidly (180°–215°/0.6 mm) giving 17.2 g of an oily epimeric mixture. Treatment of this oil in ether with excess ethereal hydrogen chloride and trituration of the precipitated salt with acetone gave 5.8 g of essentially pure axial epimer, methyl (2-exo-3-endo)-8-methyl-2(3-benzyloxyphenyl)-8-azabicyclo[3.2.1]octane-3-carboxylate hydrochloride, m.p. 209° C.(decompn.), plates from acetonitrile.

The mother liquor from separation of the axial epimer was shown by NMR to contain 85% of the equatorial epimer. The oily base from this liquor crystallized. It was recrystallized from MeOH to give 6.78 g. of methyl (exo,eco)-8-methyl-2-(3-benzyloxyphenyl)-8-azabicyclo[3.2.1]octane-3-carboxylate, m.p. 93°–94.5° C., needles from methanol.

EXAMPLE 3

Following the procedure of Example 1(a), mixture of C-3 epimers was prepared from 18.1 g (0.10 mol) of unsaturated compound IV (R and R' are methyl) and a Grignard reagent made from 24.5 g (0.15 mol) of 2-bromothiophene and 4.8 g (0.2 g-atom) of magnesium using ether as solvent. Distillation of the crude basic product gave 20.47 g (77%) of a 1:1 epimer mixture, b.p. 111°–122° C.(0.2 mm). The hydrochloride salt, formed with ethereal hydrogen chloride was triturated with acetone and then recrystallized from 35 ml of acetonitrile with cooling only to 30° C. Needle tufts separated (5.1 g) which were recrystallized from acetonitrile to give methyl (1RS-exo,exo)-8-methyl-2-(2-thienyl)-8-azabicyclo[3.2.1]octane-3-carboxylate hydrochloride, plates, m.p. 197°–198° C.

Concentration of the mother liquor from separation of the exo epimer gave 5.9 g of a mixture of needles and plates. Recrystallization of this solid from acetone afforded 5.0 g of a 45:55 mixture of hydrochlorides of the exo- and endo-esters, respectively, m.p. 168°–169° C.

When a crude, distilled, epimeric mixture obtained as above (92.6 g) was dissolved in 400 ml of methanol, treated with 2.9 g of sodium methoxide and refluxed for 3.5 hrs. under n$_2$, removal of the solvent and extraction of the basic ester with ether gave 92 g of a sticky crystalline mixture which (by NMR) contained 95% of the exo (equatorial) ester and 5% of the endo (axial) epimer. It was placed in a funnel and 125 ml of 1:1 ether-pentane was percolated through it, thereby leaving 74.9 g of essentially pure exo-epimer. Concentration of the percolate to a 25 ml volume and cooling gave 8.34 g more exo-epimer (total of 83.3 g, 96%).

EXAMPLE 4

(a) Diethyl 1-[(exo,exo)-3-Methoxycarbonyl-2-(2-thienyl)-8-azabicyclo[3.2.1]octan-8-ylmethyl]-1,2-hydrazinedicarboxylate A mixture of 16.5 g (0.062 mol) of methyl (1RS-exo,exo)-8-methyl-2-(2-thienyl)-8-azabicyclo[3.2.1]octane-3-carboxylate (Example 3), 50 g (0.29 mol) of diethyl azodicarboxylate and 150 ml of dry benzene was heated under reflux for 8 hr. Later experiments revealed that 2 moles of azo-ester per mole of tropane were adequate for this reaction. The product was extracted with 35, 25 and 25 ml of ice cold 2N hydrochloric acid and each extract was washed quickly with ether and drained into a single flask containing 15 ml of concentrated ammonium hydroxide and 15 g of ice. Ether extraction of the liberated base gave 27.4 g of oily compound which was about 95% pure by TLC (silica, 3:97 i-PrNH$_2$-Et$_2$O). This product was used satisfactorily in the following reaction.

(b) A solution of 262.8 g (0.598 mol) of the adduct obtained in part (a) above in 1600 ml of methanol, 320 ml of pyridine and 500 ml of water was chilled to 15° C., divided into two portions, and each was treated with 220 ml of cold (5° C.) 47% aqueous hydrogen iodide. The resulting solutions were left at room temperature for three days and then concentrated to solid residues by warming to 60° C. in vacuo. Each residue was slurried with 175 ml of water, the slurries were filtered, and the filter cakes were washed with two 25 ml portions of water and air-dried.

Trituration of the combined crystalline solids (246 g) with a mixture of 100 ml each of concentrated ammonium hydroxide and water, agitation of the mixture with 600 ml of ether, and filtration separated 68.7 g of crystalline diethyl 1,2-hydrazinedicarboxylate. The layers of the filtrate were separated, the water layer was extracted with ether and the combined ether layers were concentrated to a residual oil in order to remove ammonia. Dilution of the oily residue with ether, addition of excess gaseous hydrogen chloride and collection of the precipitated crystalline salt gave 108.0 g (62%) of methyl exo,exo)-2-(2-thienyl)-8-azabicyclo[3.2.1]octane-3-carboxylate hydrochloride, m.p. 235°-236° C. with intumescence. Recrystallization from acetonitrile (90 ml/g and concentrated to 25% of volume) afforded a sample with m.p. 239°-240° C. (intumescence).

EXAMPLE 5

Methyl (exo,exo)-8-(2-propyl)-2-(2-thienyl)-8-azabicyclo[3.2.1]octane-3-carboxylate was prepared by stirring a mixture of 5.02 g (0.020 mol) of methyl (exo,exo)-2-(2-thienyl)-8-azabicyclo[3.2.1]octane-3-carboxylate (Example 4), 5.04 g (0.060 mol) of solid sodium bicarbonate, 6.80 g (0.040 mol) of 2-iodopropane and 35 ml of dry dimethylformamide at room temperature for 3 days. Silica TLC (3:97 i-PrNH$_2$-Et$_2$O) showed incomplete reaction. More isopropyl iodide (6.8 g) and sodium bicarbonate (5 g) were added and the mixture was heated at 60°-70° C. with stirring for 9 hrs. TLC showed complete reaction. The dimethylformamide was removed by warming in vacuo, water was added and the mixture was extracted twice with ether. Addition of ethereal hydrogen chloride precipitated a gum which crystallized upon trituration with ether. One recrystallization of the resulting 5.1 g of salt from acetone gave 3.55 g of the title compound as its hydrochloride salt, blades and plates, m.p. 230°-231° C.

EXAMPLE 6

(exo,exo)-3-Methoxycarbonyl-2-(2-thienyl)-8-azabicyclo[3.2.1]octane-8-acetamide was prepared from 4.8 g (0.019 mol) of the N-hydrogen compound of Example 4 and 7.05 g (0.038 mol) of iodoacetamide by the method used in Example 5 except that the reaction was complete at room temperature in 3 hrs. without addition of further reagents. Following removal of the dimethylformamide the residue was treated with 25 ml of water and 40 ml of chloroform. The chloroform layer was washed twice with 10 ml portions of water and once with brine, concentrated to a 20 ml volume and treated with excess 3.5 N ethereal hydrogen chloride. Trituration of the gum with a few ml of acetone and dilution with 200 ml of ether gave 6.1 g of crystalline product. Recrystallization from 250 ml of 4:1 CH$_3$CN-EtOH boiled down to a 150 ml volume gave 3.5 g of the title compound as the hydrochloride salt, m.p. 233° C.

We claim:
1. (exo,exo)-3-Methoxycarbonyl-2-(2-thienyl)-8-azabicyclo[3.2.1]octane-8-acetamide; or a pharmaceutically acceptable acid-addition salt thereof.

* * * * *

UNITED STATES PATENT AND TRADEMARK OFFICE
CERTIFICATE OF CORRECTION

PATENT NO. : 4,233,448
DATED : November 11, 1980
INVENTOR(S) : Robert L. Clarke and Sol J. Daum It is certified that error appears in the above-identified patent and that said Letters Patent are hereby corrected as shown below:

Column 5, line 19, "0.3 56" should read --0.3 to 56--; line 58, "6" should read --6 g--.

Column 6, line 22, "(exo,eco)" should read --(exo,exo)--; line 27, insert "a" before --mixture--; line 50, "$n_2$" should read --$N_2$--.

Signed and Sealed this

Twenty-fourth Day of March 1981

[SEAL]

Attest:

RENE D. TEGTMEYER

*Attesting Officer*     *Acting Commissioner of Patents and Trademarks*